United States Patent [19]

Mina et al.

[11] Patent Number: 4,870,214
[45] Date of Patent: Sep. 26, 1989

[54] ANTIOXIDANT

[75] Inventors: George L. Mina, Orangeburg, S.C.; Raymond A. Schell, Prairieville, La.

[73] Assignee: Ethyl Corporation, Richmond, Va.

[21] Appl. No.: 196,679

[22] Filed: May 20, 1988

[51] Int. Cl.$^4$ ............................................. C07C 39/12
[52] U.S. Cl. ................................................... 568/720
[58] Field of Search ......................................... 568/720

[56] References Cited

U.S. PATENT DOCUMENTS 3,644,538  2/1972  Starnes et al. ...................... 568/720
3,925,488  12/1975  Shin .................................... 568/720
4,259,534  3/1981  Gurvich et al. ..................... 568/720

FOREIGN PATENT DOCUMENTS 1252328  11/1971  United Kingdom ................ 568/720

Primary Examiner—Werren B. Lone
Attorney, Agent, or Firm—Joseph D. Odenweller

[57] ABSTRACT

Antioxidant compounds having the structure:

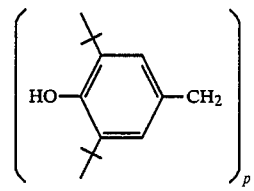

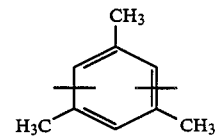

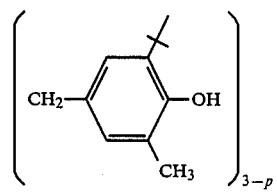

in which p is 1 or 2 and + is a tert-butyl group provide excellent oxidation stability, melt flow index and yellow index, especially in polypropylene.

14 Claims, No Drawings

ANTIOXIDANT

BACKGROUND

Phenolic antioxidants have long been used to provide oxidative stability in organic materials, especially in polymers. A very effective antioxidant is 1,3,5-tri-(3,5-di-tert-butyl-4-hydroxybenzyl)-2,4,6-trimethylbenzene described in U.S. Pat. No. 3,026,264. This product is sold by Ethyl Corporation as Ethanox ®330 Antioxidant. It is especially useful in polyolefins such as polypropylene. One problem with this additive is that it has a melt point of 240°–245° C. which is far above the melt point and normal processing temperature of many polymers. For example, polypropylene is usually processed (e.g. extruded) in a temperature range of 150°–220° C. In order to get homogenous distribution of the antioxidant in the polymer it is necessary to operate at higher temperatures than would be necessary with a lower melting antioxidant. Hence a lower melting compound which retained the excellent antioxidant properties of Ethanox ®330 Antioxidant while permitting lower temperature processing would be very beneficial.

SUMMARY

It has now been discovered that a tri-(3,5-dialkyl-4-hydroxybenzyl)mesitylene in which 1 or 2 of the 3,5-dialkyl-4-hydroxybenzyl are 3-methyl-5-tert-butyl-4-hydroxybenzyl and the other(s) is (are) 3,5-di-tert-butyl-4-hydroxybenzyl are excellent antioxidants, especially in polypropylene, and have a melting point substantially below that of the tri-(3,5-di-tert-butyl-4-hydroxybenzyl) derivative which permits processing at much lower temperature.

DESCRIPTION OF THE PREFERRED EMBODIMENTS

A preferred embodiment of the invention is a compound useful as an antioxidant in a broad range of organic materials, said compound having the structure:

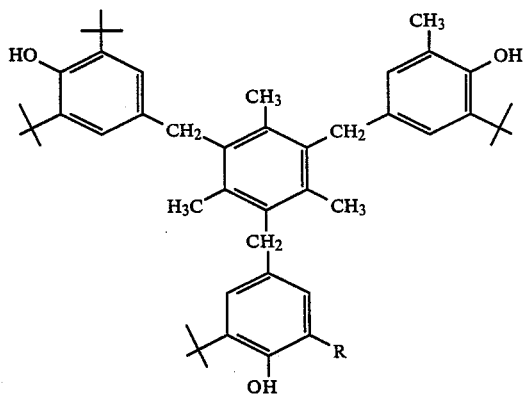

wherein R is methyl or tert-butyl and + is a tert-butyl group.

Two compounds meet the above definition. There are namely: 1,3-di-(3,5-di-tert-butyl-4-hydroxybenzyl)-5-(3-methyl-5-tert-butyl-4-hydroxybenzyl-2,4,6-trimethylbenzene and 1,3-di-(3-methyl-5-tert-butyl-4-hydroxybenzyl)-5-(3,5-di-tert-butyl-4-hydroxybenzyl)-2,4,6-trimethylbenzene. Of these the former is most preferred.

The new compounds can be made reacting about 1–2 moles of 2-methyl-6-tert-butyl-4-methoxymethylphenol with mesitylene in an inert solvent such as methylene chloride and in the presence of an acid (e.g. sulfuric acid) catalyst. This makes a mono- or di-(3-methyl-5-tert-butyl-4-hydroxybenzyl) substituted mesitylene or mixtures thereof. In a second step this intermediate is reacted with sufficient 2,6-di-tert-butyl-4-methoxymethyl phenol to complete substitution of the mesitylene. The acid layer is drained off and the resultant solution is washed with aqueous sodium carbonate to neutralize the solution. The solvent can then be removed by heating over a steam bath. The recovered product can be used as an antioxidant or it can be purified by recrystallization from an inert solvent such as isooctane.

The following example shows how the new compounds can be prepared.

EXAMPLE

In a 1 liter stainless steel autoclave was placed 440 ml methanol, 19.6 g (0.65 mole) paraformaldehyde, 5.3 g (0.048 mole) 40 percent aqueous dimethylamine catalyst and 82.4 g (0.5 mole) 2-methyl-6-tert-butylphenol. The autoclave was sealed and heated while stirring to 130° C. Stirring was continued at 130° C. for 3 hours 10 minutes. Analysis by gas chromatograph (GC) showed the reaction forming 2-methyl-6-tert-butyl-4-methoxymethylphenol to be 95 percent complete. The mixture was transferred to a distillation flask under nitrogen and the excess methanol was distilled out up to a flask temperature of 100° C. The residue was cooled and dissolved in 290 g methylene chloride.

In a 1 liter flask was placed 100 ml methylene chloride and 24 g (0.2 moles) of mesitylene. While stirring, two solutions were concurrently fed to the stirred mesitylene solution over a one-hour period while maintaining the temperature at 5° C. with an ice bath. One solution was 100 g of the solution of 2-methyl-6-tert-butyl-4-methoxymethylphenol in methylene chloride prepared above (0.116 moles). The second solution was 41.7 g of 84 percent H$_2$SO$_4$. After the addition, the mixture was stirred 15 minutes and then transferred to a separatory funnel. The lower sulfuric acid phase was removed and the methylene chloride phase was water washed and then washed with 100 ml 5 percent aqueous sodium carbonate and finally 2 more times with water. The methylene chloride was then distilled out using a rotary evaporator. The residue, mainly mono-3-methyl-5-tert-butyl-4-hydroxybenzyl)mesitylene was then re-dissolved in 100 ml methylene chloride. This solution was transfered to a 1 liter reaction flask. While stirring at 5° C., the following 2 solutions were fed concurrently. The first was a solution of 78 g (0.31 moles) of 2,6-di-tert-butyl-4-methoxymethylphenol (prepared as above but using 2,6-di-tert-butylphenol) in 182 g of methylene chloride. The second solution was 70 g of 84 percent sulfuric acid. The resulting mixture was stirred 15 minutes and then transferred to a separatory funnel, the lower H$_2$SO$_4$ phase drained out. Then 7 g of sodium carbonate was dissolved in 240 g deionized water and this solution added to the separated product-methylene chloride solution. This mixture was placed in a distillation flask and the methylene chloride was distilled out leaving the solid product in the aqueous phase. Heptane was added to extract the solid product. The aqueous phase was separated and the hot heptane solution was washed twice with 200 ml water. The heptane solution was slowly cooled to 5° C. and the solids which separated were filtered off. The white precipitate was washed with 40 ml cold heptane leaving 31 g of white solid produce (m.p. 141°–147° C.). Analysis by GC showed the product to be 97 percent 1,3-di-(3,5-di-tert-butyl-4-hydroxy-benzyl-5-(3-methyl-5-tert-butyl-4-hydroxybenzyl)-2,4,6-rimethyl-benzene. This was recrystallized from isooctane which raised the melt point to 194°–196° C.

The above procedure can be used to make 1,3-di-(3-methyl-5-tert-butyl-4-hydroxybenzyl-5-(3,5-di-tert-butyl-4-hydroxylbenzyl)-2,4,6-trimethylbenzene by increasing the ratio of 2-methyl-6-tert-butyl-4-methoxymethylphenol to mesitylene to abou 2:1. Likewise mixtures can be made by proper adjustment of the ratio between about 1:2 to 2:1.

Tests were conducted which demonstrate the effectiveness of the present additives. One such test was an oven-aging test in which the new additive was directly compared to the symmetrical 1,3,5-tris(3,5-di-tert-butyl-4-hydroxybenzyl)-2,4,6-trimethylbenzene n a polyproylene substrate. Polypropylene powder was blended with calcium stearate and the test antioxidant. Some formulations also included distearylthiodipropionate (DSTDP). The blend was then passed through a twin screw extruder to form homogenous samples. These are molded into test specimen about 20 mils thick (2.5 x 1.25 cm). Five replicates were made of each blend. The replicates were placed in an oven at 150° C. Failure was when 3 of the 5 replicates show visible signs of degration (e.g. crazing, cracking, powdering). The test results are shown in the following table.

| Sample | Conc(ppm) | Days to Failure |
| --- | --- | --- |
| A. prior art[1] | 500 | 10 |
| calcium stearate | 500 | |
| B. the invention[2] | 500 | |
| calcium stearate | 500 | 14 |
| C. prior art[1] | 500 | |
| calcium stearate | 500 | |
| DSTDP | 1500 | 51 |
| D. the invention[2] | 500 | |
| calcium stearate | 500 | |
| DSTDP | 1500 | 61 |

[1]1,3,5-tri(3,5-di-tert-butyl-4-hydroxybenzyl)-2,4,6-tri-methylbenzene.
[2]1-(3-methyl-5-tert-butyl-4-hydroxybenzyl)-3,5-di-(3,5-di-tert-butyl-4-hydroxybenzyl)-2,4,6-trimethylbenzene.

The results clearly show that Samples B and D of the invention are substantially more stable than Samples A and C containing the prior art commercial antioxidant.

The new compounds of the invention are particularly useful as antioxidants. The antioxidants can be used in a broad range of organic material normally subject to gradual degradation in the presence of oxygen during use over an extended period. In other words, the organic materials protected by the present antioxidants are of the type in which the art recognizes the need for antioxidant protection and to which an antioxidant of some type is customarily added to obtain an extended service life. The oxidative degradation protected against is the deterioration of the organic composition during or after processing rather than, for example, combustion.

Examples of organic materials in which the antioxidants of this invention are useful include polymers, both homopolymers and copolymers, of olefinically unsaturated monomers, for example, polyolefins such as polyethylene, polypropylene, polybutylene and the like including linear low density polyethylene (LLDPE) and high density polyethylene (HDPE).

Also, polyhalohydrocarbons such as polyvinyl chloride, polychloroprene, polyvinylidene chloride, polyfluoroolefins, and the like, are afforded stabilization. The antioxidants provide antioxidant protection in natural and synthetic rubbers such as copolymers of olefinically unsaturated monomers including styrene-butadiene rubber (SBR rubber), ethylene-propylene copolymers, ethylene-propylene-diene terpolymers such as the terpolymer of ethylene, propylene and cyclopentadiene or 1,4-cyclooctadiene. Polybutadiene rubbers such as cis-poly-butadiene rubber are protected. Poly-2-2chloro-1,3-butadiene (neoprene) and poly-2-methyl-1,3-butadiene (isoprene rubber) are stabilized by the present additives. Likewise, acrylonitrile-butadiene-styrene (ABS) resins are effectively stabilized. Ethylene-vinyl acetate copolymers (EVA) are protected, as are butene-methylacrylate copolymers. Nitrogen-containing polymers such as polyurethanes, polyureas, nitrile rubber, and lauryl acrylate-vinyl pyrrolidone copolymers are effectively stabilized. Adhesive compositions such as solutions of polychloroprene (neoprene) in toluene are protected. Polyphenylene ethers such as poly-2,6-dimethyl-1,4-phenylene ethers either alone or in combination with blending agents such synthetic rubbers are protected by the present invention. Likewise polystyrene and rubber modified polystyrene (i.e., high impact polystyrene) are stabilized.

Petroleum oils such as solvent-refined, midcontinent lubricating oil and Gulf Coast lubricating oils are effectively stabilized. In hydrocarbon lubricating oils, both mineral and synthetic, the present antioxidants are effective when used in combination with a zinc dihydrocarbyl dithiophosphate e.g. zinc dialkyl dithiophosphate or zinc dialkaryl dithiophosphate.

Other petroleum products that can be stabilized include distillate fuels (e.g., gasoline), petroleum wax, asphalt, tar, grease and the like.

Synthetic ester lubricants such as those used in turbines and turbojet engines are given a high degree of stabilization. Typical synthetic ester lubricants include di-2-ethylhexyl sebacate, trimethylolpropane tripelargonate, $C_{5-9}$ aliphatic monocarboxylic esters of pentaerythritol, complex esters formed by condensing under esterifying conditios, mixtures of polyols, polycarboxylic acids, and aliphatic monocarboxylic acids and/or monohydric alkanols. An example of these complex esters is the condensation product formed from adipic acid, ehtylene glycol and a mixture of $C_{5-9}$ aliphatic monocarboxylic acids. Plasticizers such as dioctyl phthalate are effectively protected. Heavy petroleum fractions such as tar and asphalt can also be protected should the need arise.

Polyamides such as adipic acid-1,6-diaminohexane condensates and poly-6-aminohexanoic acid (nylon) are effectively stabilized. Polyalkylene oxides such as copolymers or phenol with ethylene oxide or propylene oxide are stabilized. Polyphenylene ethers such as poly-2,6-dimethylphenylene ether formed by polymerizationof 2,6-dimethylphenol using a copper-pyridine catalyst are stabilized. Polycarbonate plastics and polyformaldehydes are also protected.

Linear polyesters such as phthalic anhydride-glycol condensates, poly[ethylene terephthalate] (PET), and poly[butylene terephthalate] (PBT), are given a high degree of protection. Other polyesters such as trimellitic acid-glycerol condensates are also protected. Polyacrylates such as polymethylacrylat and polymethylmethacrylate are effectively stabilized. Polyacrylonitriles and copolymers of acrylonitriles with other olefinically unsaturated monomers such as methylmethacrylates are also effectively stabilized as are polyorganophosphazenes, e.g., polyaryloxyphosphazene.

The antioxidants of the present invention are preferably used in either thermoset or thermoplastic polymer compositions. The thermoset polymers are those plastics which when subjected to heat, will normally become infusible or insoluble and as such cannot be remelted. They have elaborately cross-linked three dimensional structures.

In contrast to the thermoset polymers, most thermoplastic polymers can be made to soften and take a new shape by the application of heat and pressure. Thermoplastic polymers comprise long-chain molecules often without any branching (e.g., high density polyethylene). Thermoplastic polymers normally are rigid at operating temperatures, but can be remelted and reprocessed. They include polyethylene, polycarbonate, polypropylene, polystyrene, polyvinyl chloride, acrylonitrile-butadiene-styrene butadiene-styrene (ABS), nylon, and the like, including polymers intended for high temperature applications. The most preferred organic compositions intended for the practice of the present invention are the polymers of olefinically unsaturated monomers including homopolymers and copolymers of two or more of such monomers. The most preferred organic composition is a homopolymer or copolymer of ethylene and/or propylene.

The more preferred utility of the new additives is in the stabilizationof thermoplastic polymers during processing such as during extrusion. Of these the most preferred polymers are polyethylene, polypropylene, linear low density polyethylene and polycarbonates.

The antioxidants of the present invention are useful to control oxidative and color degradation of resins used as tackifiers in adhesives. The resin which can be protected include synthetic hydrocarbon resins, such as cycloaliphatic $C_5$ resins, aromatic $C_9$ resins, terpene resins and the like. Also included are natural resins, such as wood rosin, gum rosin and tall oil rosin which are processed for tackifier applications.

The antioxidants are incorporated into the organic material in a small but effective amount so as to provide the required antioxidant protection. A useful range is generally from about 0.005 to about 5 weight percent of organic material, and a preferred range is from about 0.01 to 2 weight percent. The antioxidants are preferably used in combination with about 0.001-5 weight percent of a synergist such as dilauryl thiodipropionate or distearyl thiodipropionate.

Methods of incorporating the antioxidants into the organic material are well known. For example, if the material is liquid, the additive can be merely mixed into the material. Solid organic materials can be merely sprayed with a solution of the additive in a volatile solvent. For example, stabilized grain products result from spraying the grain with a toluene solution of the antioxidant. In the case of rubbery polyers, the additive can be added following the polymerization stage by mixing it with the final emulsion or solution polymerization mixture and then coagulating or removing solvent to recover the stabilized polymer. It can also be added at the compounding stage by merely mixing the additive with the rubbery polymer in commercial mixing equipment such as a Banbury blender. In this manner, rubbery polymers such as styrene-butadiene rubber, cis-polybutadiene or isoprene polymers are blended with the antioxidant together with the other ingredients normally added such as carbon black, oil sulfur, zinc oxide, stearic acid, vulcanization accelerators, and the like. Following mastication, the resultant mixture is fabricated and molded into a finished form and vulcanized.

What is claimed is:

1. A compound useful as an antioxidant in a broad range of organic materials, said compound having the structure:

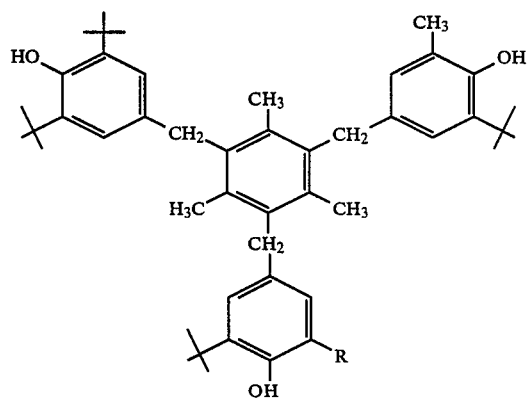

wherein R is methyl or tert-butyl and +is a tert-butyl group.

2. A compound of claim 1, namely: 1,3-di-(3,5-di-tert-butyl-4-hydroxybenzyl)-5-(3-methyl-5-tert-butyl-4-hydroxybenzyl)-2,4,6-trimethylbenzene.

3. A compound of claim 1, namely: 1,3-di(3-methyl-5-tert-butyl-4-hydroxybenzyl)-5-(3,5-di-tert-butyl-4-hydroxybenzyl)-2,4,6-trimethylbenzene.

4. An organic composition normally subject to gradual degradation under use conditions due to the effect of atmospheric oxygen, said composition containing an antioxidant amount of a compound of claim 1.

5. A composition of claim 4 wherein said compound is 1,3-di-(3-methyl-5-tert-butyl-4-hydroxybenzyl)-5-(3,5-di-tert-butyl-4-hydroxybenzyl)-2,4,6-trimethylbenzene.

6. A composition of claim 4 wherein said compound is 1,3-di-(3-methyl-5-tert-butyl-4-hydroxybenzyl)-5-(3,5-di-tert-butyl-4-hydroxybenzyl)-2,4,6-trimethylbenzene.

7. A composition of claim 4 wherein said organic composition is a polymer of an olefinically unsaturated monomer.

8. A composition of claim 7 wherein said polymer is a homopolymer or copolymer of an olefinic hydrocarbon.

9. A composition of claim 8 wherein said polymer is a homopolymer or copolymer of ethylene.

10. A composition of claim 8 wherein said polymer is a homopolymer or copolymer of propylene.

11. A composition of claim 8 wherein said compound is 1,3-di-(3,5-di-tert-butyl-4-hydroxybenzyl)-5-(3-methyl-5-tert-butyl-4-hdroxybenzyl)-2,4,6-trimethylbenzene.

12. A composition of claim 11 wherein said polymer is a homopolymer or copolymer of propylene.

13. A composition of claim 8 wherein said compound is 1,3-di-(3-methyl-5-tert-butyl-4-hydroxybenzyl)-5-(3,5-di-tert-butyl-4-hydroxybenzyl)-2,4,6-trimethylbenzene.

14. A composition of claim 13 wherein said polymer is a homopolymer or copolymer or propylene.

* * * * *

UNITED STATES PATENT AND TRADEMARK OFFICE
CERTIFICATE OF CORRECTION

PATENT NO. : 4,870,214

DATED : SEPTEMBER 26, 1989

INVENTOR(S) : GEORGE L. MINA ET AL.

It is certified that error appears in the above-identified patent and that said Letters Patent is hereby corrected as shown below:

Column 6, line 59 reads "hdroxybenzyl)" and should read -- hydroxybenzyl) -- .

Signed and Sealed this

Twenty-fifth Day of September, 1990

Attest:

HARRY F. MANBECK, JR.

*Attesting Officer*     *Commissioner of Patents and Trademarks*